US006941165B2

(12) United States Patent
Nakai et al.

(10) Patent No.: US 6,941,165 B2
(45) Date of Patent: Sep. 6, 2005

(54) CARDIAC MAGNETIC FIELD DIAGNOSING APPARATUS BY LATE VENTRICULAR POTENTIAL AND METHOD OF LOCATING INTRAMYOCARDIAL EXCITEMENT UNEVEN PROPAGATION PORTION

(75) Inventors: Kenji Nakai, Morioka (JP); Masahito Yoshizawa, Morioka (JP); Kohei Kawazoe, Morioka (JP); Keita Yamazaki, Inzai (JP); Satoshi Fujita, Osaka (JP); Itsuro Tamura, Osaka (JP)

(73) Assignees: Japan Science and Technology Corporation, Saitama (JP); Takenaka Corporation, Osaka (JP)

(*) Notice: Subject to any disclaimer, the term of this patent is extended or adjusted under 35 U.S.C. 154(b) by 0 days.

(21) Appl. No.: 10/333,056

(22) PCT Filed: Jul. 17, 2001

(86) PCT No.: PCT/JP01/06194

§ 371 (c)(1),
(2), (4) Date: Oct. 14, 2003

(87) PCT Pub. No.: WO02/05715

PCT Pub. Date: Jan. 24, 2002

(65) Prior Publication Data

US 2004/0049119 A1 Mar. 11, 2004

(30) Foreign Application Priority Data

Jul. 18, 2000 (JP) ........................................ 2000-217835

(51) Int. Cl.⁷ ................................................. A61B 5/04
(52) U.S. Cl. ..................................................... 600/509
(58) Field of Search ............................... 600/409, 509, 600/512, 513, 515, 516, 517, 524, 525, 523, 518

(56) References Cited

U.S. PATENT DOCUMENTS 5,136,242 A * 8/1992 Abraham-Fuchs .......... 324/244

(Continued)

FOREIGN PATENT DOCUMENTS

EP 0968683 A1 1/2000

(Continued)

OTHER PUBLICATIONS

Robinson, S.E. et al., "Functional Neuroimaging by Synthetic Aperture Magnetometry (SAM)," Proceedings of the 11th International Conference on Biomagnetism, "Recent Advances in Biomagnetism," Tohoku University Press, 1999, pp. 302–305.

(Continued)

Primary Examiner—Jeffrey R. Jastrzab
(74) Attorney, Agent, or Firm—Birch, Stewart, Kolasch & Birch, LLP

(57) ABSTRACT

A magnetic field distribution measurement device (1) provides a non-contact magnetic measurement on a subject's chest at a plurality of coordinates and forms therefrom time-series magnetic field distribution data. A first arithmetic device (2) in response generates image data representing an intramyocardial excitation conduction rate. A second arithmetic device (3) receives a plurality of tomographic image data separately obtained by a tomographic diagnosis apparatus and processes the data to generate three-dimensional, anatomical image data. A display device (4) receives these data and displays on an anatomical image an image representing an intramyocardial excitation current. This can facilitate identifying an anatomical, positional relationship of a ventricular late potential caused in heart muscle. Furthermore, the anatomical image may be replaced with an image representing a normal stimulation conduction path and serving as a template.

14 Claims, 13 Drawing Sheets

U.S. PATENT DOCUMENTS

| | | | | |
|---|---|---|---|---|
| 5,341,811 A | * | 8/1994 | Cano | 600/508 |
| 5,694,942 A | * | 12/1997 | Escalona | 600/509 |
| 5,827,195 A | * | 10/1998 | Lander | 600/509 |
| 6,187,032 B1 | * | 2/2001 | Ohyu et al. | 600/409 |
| 6,473,518 B1 | * | 10/2002 | Machida et al. | 382/128 |
| 6,527,724 B1 | * | 3/2003 | Fenici | 600/466 |
| 6,539,245 B2 | * | 3/2003 | Tsukada et al. | 600/409 |
| 2004/0054335 A1 | * | 3/2004 | Lesh et al. | 604/264 |

FOREIGN PATENT DOCUMENTS

| | | | | | |
|---|---|---|---|---|---|
| JP | 5-157735 A | | 6/1993 | | |
| JP | 5-220124 | * | 8/1993 | | A61B/5/05 |
| JP | 8-289877 A | | 11/1996 | | |
| JP | 10-276998 A | | 10/1998 | | |
| JP | 10-323335 A | | 12/1998 | | |
| JP | 11-128191 A | | 5/1999 | | |
| JP | 11-128224 A | | 5/1999 | | |
| JP | 2001-112732 | * | 10/1999 | | A61B/5/055 |
| WO | WO 98/15226 A1 | | 4/1998 | | |

OTHER PUBLICATIONS

Hara, K. et al., "Science of Cerebric Magnetic Field—SQUID Measurement and Medical Applications," Ohmsha, Jan. 25, 1997, pp. 117–119 (with partial translation).

Ueda, T. et al., "Visualization of Source Current Distribution in Human Heart based on Magnetocardiogram Data," $9^{th}$ Digital Signal Processing Symposium, Nov. 10–11, 1994, pp. 307–312.

* cited by examiner

F I G. 1 1
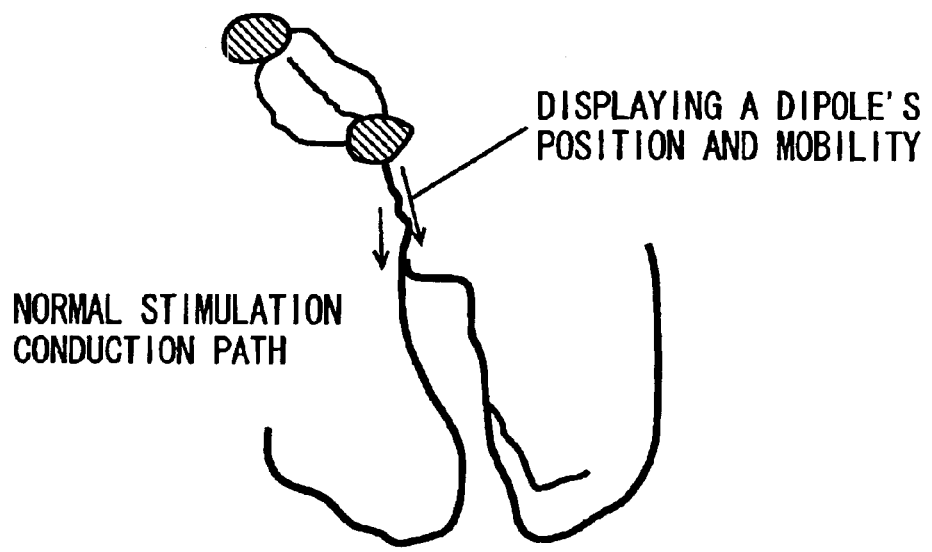

CARDIAC MAGNETIC FIELD DIAGNOSING APPARATUS BY LATE VENTRICULAR POTENTIAL AND METHOD OF LOCATING INTRAMYOCARDIAL EXCITEMENT UNEVEN PROPAGATION PORTION

TECHNICAL FIELD

The present invention relates generally to magnetocardiographic diagnosis apparatuses for a ventricular late potential and methods of identifying a part in myocardium providing un-uniform conduction of excitation, and particularly to such apparatuses and methods employing a non-contact magnetic measurement to non-invasively diagnose a three-dimensional location of a ventricular late potential, or a part in myocardium providing un-uniform conduction of excitation that might cause ventricular tachycardia.

BACKGROUND ART

Conventionally, recording electrocardiograms has been generally adopted as a technique to diagnose heart diseases.

However, conventional electrocardiography is insufficient for example to determine the location, size and geometry of a part to be treated in a heart surgery and it cannot satisfactorily locate an affected part.

This is attributed to the fact that electrocardiography is an indirect measurement methodology. Different subjects have different tissues existing between their hearts and body surfaces, different positional relationships between their hearts and other organs and bones, their respective hearts having different sizes, a different electric conductance for each tissue of their bodies, and the like. As such, it has been significantly difficult to accurately determine an affected part from information obtained from indirect measurement such as electrocardiography.

A recent study has revealed that a macular texture that is formed in a normal myocardial tissue a period of time after the onset of myocardial infarction or attributed to cardiomyopathy or other similar heart diseases induces ventricular tachycardia.

Macular texture refers to a normal myocardial tissue with a necrosed or degenerated tissue existing therein in the form of an island. In such a part of myocardium, un-uniform conduction of excitation is caused and a ventricular late potential is generated. Furthermore in such a macular texture a necrosed or degenerated tissue and a normal tissue have different electrical conduction characteristics and accordingly a double excitation conduction path (a reentry circuit) can be formed.

More specifically, an excitation signal would circle in this reentry circuit and as a result ventricular tachycardia is induced. Accordingly there exists a strong demand for three-dimensionally, accurately identifying such a part having a ventricular late potential.

Electrocardiography allows electrocardiography synchronization addition to be used to non-invasively detect whether a ventricular late potential is present or absent. However, as has been described above, it has been unable to three-dimensionally identify localization of a part in myocardium providing un-uniform conduction of excitation. An attempt has also been made to use multi-channel, electrocardiographically measured data to determine the location, size and geometry of a part having a ventricular late potential. It is, however, insufficient in precision to so determine the location and thus hardly satisfactory.

Currently, endocardial mapping using a catheter, which is a type of invasive test, is employed to observe fragmented activity to identify a part in myocardium providing un-uniform conduction of excitation. In particular, a methodology has been adapted that uses a catheter to conduct an electrophysiological test to identify a part in myocardium providing un-uniform conduction of excitation and furthermore provide a treatment by catheter with a high frequency hypersthenia (catheter ablation).

In this methodology, however, the catheter is inserted and moved while chest x-ray fluoroscopy is effected. Consequently, patients, doctors and radiographers are exposed to x-ray radiation over long periods of time. In particular, doctors and radiographers suffer large annual doses of x-ray radiation. Accordingly, there has been a strong demand for significantly reducing the time required for conducting such a test.

In a variety of fields a superconducting quantum interference device (SQUID) magnetometer has been applied. It uses an SQUID capable of detecting with high sensitivity a magnetic flux of one billionth of geomagnetism. In particular, in the field of somatometry, which strongly demands non-invasive measurement, as described above, an attempt is being made to use a SQUID magnetometer to provide a non-contact magnetic measurement of human bodies.

In particular, the development of thin-film device fabrication technology in recent years has allowed the development of a DC-SQUID, and an attempt is being made to use a SQUID magnetometer to measure a magnetocardiogram, a distribution of a magnetic field of a heart.

However, a magnetocardiogram alone cannot directly display the location, size, and geometry of a part in myocardium providing un-uniform conduction of excitation, and it hardly allows doctors to correctly understand a relative, positional relationship of an affected part in a heart.

Accordingly it has been proposed to visualize an intramyocardial, electric current behavior from a magnetocardiographic distribution represented in a magnetocardiogram. One such approach adopted is to use one or more small current element pieces (current dipoles) to mimic the source of a magnetic field for visualization. This methodology has been confirmed to be effective in determining the position of a bypass circuit (a secondary conduction path) having-peculiar electrophysiological characteristics in the WPW syndrome, e.g., a Kent bundle.

On the other hand, it has been confirmed that an excitation conduction path extending from a sinoauricular node to an atrioventricular node-a bundle of His-Purkinje fiber network can be represented by a method using the above-described current dipole to determine a source of a signal.

However, using one or more current dipoles to mimic a source of a magnetic field for visualization can only provide positional information of the current dipole(s) corresponding to a specific time point and it cannot three-dimensionally identify the location, size and geometry of a part in myocardium that has a ventricular late potential, i.e., a part in myocardium providing un-uniform conduction of excitation.

The present invention therefore contemplates an magnetocardiographic diagnosis apparatus for a ventricular late potential and a method of identifying a part in myocardium providing un-uniform conduction of excitation that can employ a non-invasive magnetic measurement to provide data representative of an intramyocardial, three-dimensional, electrical behavior and used to safely, rapidly and with high precision, three-dimensionally identify a positional relationship of a part in myocardium that has a ventricular late potential, i.e., a part in myocardium providing un-uniform conduction of excitation.

DISCLOSURE OF THE INVENTION

In accordance with the present invention a magnetocardiographic diagnosis apparatus for ventricular late potential includes a magnetic field distribution measurement device, a first arithmetic device, a second arithmetic device and a display device. The magnetic field distribution measurement device performs a non-contact magnetic measurement on a subject's chest at a plurality of coordinates to obtain a plurality of time-series magnetic data corresponding to the plurality of coordinates, and also using the plurality of time-series magnetic data to generate time-series magnetic field distribution data on the chest. The first arithmetic device uses the generated time-series magnetic field distribution data to generate data representative of a three-dimensional, intramyocardial, electrical behavior of the subject. The second arithmetic device processes separately provided, tomographic, thoracic data of the subject to generate data representative of an anatomical image. The display device displays an image of the three-dimensional, intramyocardial, electrical behavior represented by the data generated by the first arithmetic device, as superimposed on the anatomical image represented by the data generated by the second arithmetic device, thereby capable of three-dimensionally identifying localization of a ventricular late potential attributed to intramyocardial, un-uniform conduction of excitation.

Preferably the data generated by the first arithmetic device and representative of the three-dimensional, intramyocardial, electrical behavior is data representative of an intramyocardial excitation conduction rate.

More preferably the first arithmetic device approximates by means of one or more small current element pieces a part in myocardium corresponding to an excitation conduction path and calculates a temporal variation of a position of the small current element piece to generate data representative of an intramyocardial excitation conduction rate.

Still more preferably the first arithmetic device operates based on the calculated temporal variation of the position of the small current element piece to generate data representative of a difference in intramyocardial excitation conduction rate for each excitation conduction path.

In accordance with the present invention in another aspect a magnetocardiographic diagnosis apparatus for ventricular late potential includes a magnetic field distribution measurement device, an arithmetic device and a display device. The magnetic field distribution measurement device performs a non-contact magnetic measurement on a subject's chest at a plurality of coordinates to obtain a plurality of time-series magnetic data corresponding to the plurality of coordinates, and also using the plurality of time-series magnetic data to generate time-series magnetic field distribution data on the chest. The arithmetic device uses the generated time-series magnetic field distribution data to generate data representative of a three-dimensional, intramyocardial, electrical behavior of the subject. The display device uses the data generated by the arithmetic device to superimpose together an image representing a stimulation conduction path of the subject extending from a sinoatrial node to a bundle of His-Purkinje fiber network and an image representing a three-dimensional, intramyocardial, electrical behavior and display the images, thereby capable of three-dimensionally identifying localization of a ventricular late potential attributed to intramyocardial, un-uniform conduction of excitation.

Preferably the data generated by the arithmetic device and representative of the three-dimensional, intramyocardial, electrical behavior is data representative of an intramyocardial excitation conduction rate.

More preferably the arithmetic device approximates by means of one or more small current element pieces a part in myocardium corresponding to an excitation conduction path and calculates a temporal variation of a position of the small current element piece to generate data representative of the intramyocardial excitation conduction rate.

Still more preferably the arithmetic device operates based on the calculated temporal variation of the position of the small current element piece to generate data representative of a difference in intramyocardial excitation conduction rate for each excitation conduction path.

In accordance with the present invention in still another aspect a method of identifying a part in myocardium providing un-uniform conduction of excitation includes the steps of: performing a non-contact magnetic measurement on a subject's chest at a plurality of coordinates to obtain a plurality of time-series magnetic data corresponding to the plurality of coordinates and used to generate time-series magnetic field distribution data of the chest and generating first data representative of a three-dimensional, intramyocardial, electrical behavior of the subject from the generated time-series magnetic field distribution data; processing separately fed, tomographic, thoracic image data of the subject to generate second data representative of an anatomical image; and displaying an image of the three-dimensional, intramyocardial, electrical behavior represented by the first data, as superimposed on the anatomical image represented by the second data, to allow three-dimensional identification of localization of a ventricular late potential attributed to intramyocardial, un-uniform conduction of excitation.

Preferably the three-dimensional, intramyocardial, electrical behavior represented by the first data is an intramyocardial excitation conduction rate.

More preferably the step of generating the first data uses one or more small current element pieces to approximate a part in myocardium corresponding to an excitation conduction path and calculates a temporal variation of a position of the small current element piece to generate data representative of the intramyocardial excitation conduction rate.

Still more preferably the step of generating the first data uses the calculated temporal variation of the position of the small current element piece to generate data representative of a difference in excitation conduction rate for each excitation conduction path.

In accordance with the present invention in still another aspect a method of identifying a part in myocardium providing un-uniform conduction of excitation includes the steps of: performing a non-contact magnetic measurement on a subject's chest at a plurality of coordinates to obtain a plurality of time-series magnetic data corresponding to the plurality of coordinates and used to generate time-series magnetic field distribution data of the chest and generating data representative of a three-dimensional, intramyocardial, electrical behavior of the subject from the generated time-series magnetic field distribution data; and using the generated data to superimpose together an image representing a stimulation conduction path of the subject extending from a sinoatrial node to a bundle of His-Purkinje fiber network and an image representing a three-dimensional, intramyocardial, electrical behavior, and thus displaying the images to allow three-dimensional identification of localization of a ventricular late potential attributed to intramyocardial, un-uniform conduction of excitation.

Preferably the three-dimensional, intramyocardial, electrical behavior represented by the data is an intramyocardial excitation conduction rate.

More preferably the step of generating the data uses one or more small current element pieces to approximate a part in myocardium corresponding to an excitation conduction path and calculates a temporal variation of a position of the small current element piece to generate data representative of the intramyocardial excitation conduction rate.

Still more preferably the step of generating the data uses the calculated temporal variation of the position of the small current element piece to generate data representative of a difference in the intramyocardial excitation conduction rate of each excitation conduction path.

Thus in accordance with the present invention an image representing a three-dimensional, intramyocardial, electrical behavior obtained from a non-invasive magnetic measurement that is superimposed on anatomical image obtained by processing the same subject's tomographic, thoracic image data obtained by a separate, medical diagnosis apparatus can be displayed to allow doctors to safely, rapidly and with high precision identify localization of a part having a ventricular late potential, i.e., a part in myocardium providing un-uniform conduction of excitation that might cause ventricular tachycardia.

Furthermore in accordance with the present invention an image representing a three-dimensional, intramyocardial, electrical behavior obtained from a non-invasive magnetic measurement that is superimposed on an image of a stimulation conduction path in the same subject extending from a sinoauricular node to a bundle of His-a Purkinje fiber network can be displayed to allow doctors to safely, rapidly and with high precision identify localization of a part having a ventricular late potential, i.e., a part in myocardium providing un-uniform conduction of excitation that might cause ventricular tachycardia.

BRIEF DESCRIPTION OF THE DRAWINGS

In the drawings:

FIG. 11 shows an image of a normal stimulation conduction path and an excitation conduction path, as displayed on a display device 6.

BEST MODES FOR CARRYING OUT THE INVENTION

Figure 1:
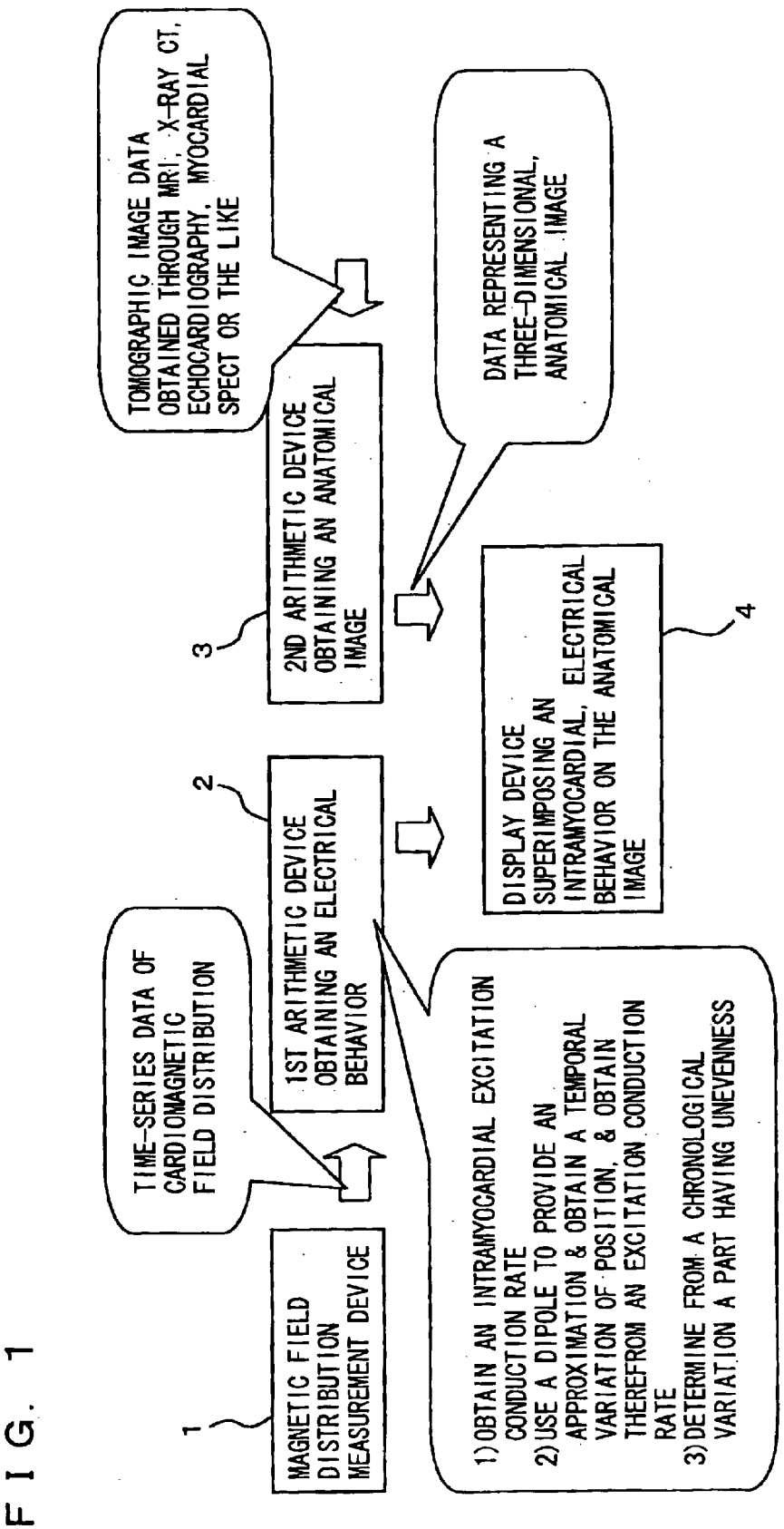
FIG. 1 is a functional block diagram schematically showing a configuration of a magnetocardiographic diagnosis apparatus for ventricular late potential in accordance with the present invention in a first embodiment.

Hereinafter, the present invention in embodiments will specifically be described with reference to the drawings. Note that in the figures, like components are denoted by like reference characters and their descriptions will not be repeated.

First Embodiment

FIG. 1 is a functional block diagram schematically showing a configuration of a magnetocardiographic diagnosis apparatus for ventricular late potential in accordance with the present invention in a first embodiment.

As shown in FIG. 1, a magnetic field distribution measurement device 1 for example uses a measurement means such as a SQUID magnetometer, as will be described hereinafter more specifically, to provide a non-contact magnetic measurement on a subject's chest at a plurality of coordinates to obtain a plurality-of time-series magnetic data corresponding to the plurality of coordinates. The plurality of time-series magnetic data are then used to generate and output time-series magnetic field distribution data of a magnetic field existing on the subject's chest, i.e., of the subject's heart.

The cardiac, time-series magnetic field distribution data provided by magnetic field distribution measurement device 1 is used by a first arithmetic device 2 for example employing a known calculation technique, as described hereinafter, to generate and output first data representing a three-dimensional, intra-myocardial electrical behavior.

More specifically, the first arithmetic device 2 generates data representing an intramyocardial excitation conduction rate. This rate is obtained, as will be described hereinafter, by using one or more small current element pieces, or current dipoles, to approximate a part in myocardium that corresponds to an excitation conduction path, and calculating the dipole/dipoles positional variation with time. From the calculated variation, data of an excitation conduction rate can be obtained for each excitation conduction path. Consequently, localization of a ventricular late potential attributed to un-uniform conduction of excitation can be determined.

Furthermore, magnetic resonance imaging (MRI), x-ray, computed tomography (CT), echocardiography, myocardial, single photon emission computed tomography (SPECT) or any other similar tomographic diagnosis apparatus is used to separately obtain tomographic, thoracic image data (including data of a plurality of tomographic images) of the same subject. The data are fed to a second arithmetic device 3 and processed thereby to generate and output second data representing a three-dimensional, anatomical image.

If the first data is represented in an image, and an electrical behavior obtained in the first arithmetic device 2 corresponds to an intramyocardial excitation conduction rate, then by noting un-uniformity of an intramyocardial excitation conduction rate for each excitation conduction path displayed on a screen in some form, a part having a ventricular late potential can be three-dimensionally identified.

Display device 4 superimposes an image representing a three-dimensional, intramyocardial electrical behavior (e.g., an excitation conduction rate of each excitation conduction path) represented by the first data generated by the first arithmetic device, on a three-dimensional, anatomical image of a subject's chest that is represented by the second data generated by the second arithmetic device 3, and displays the same. As a result, on an anatomical image, localization of a ventricular late potential in myocardium can be identified three-dimensionally.

Figure 2:
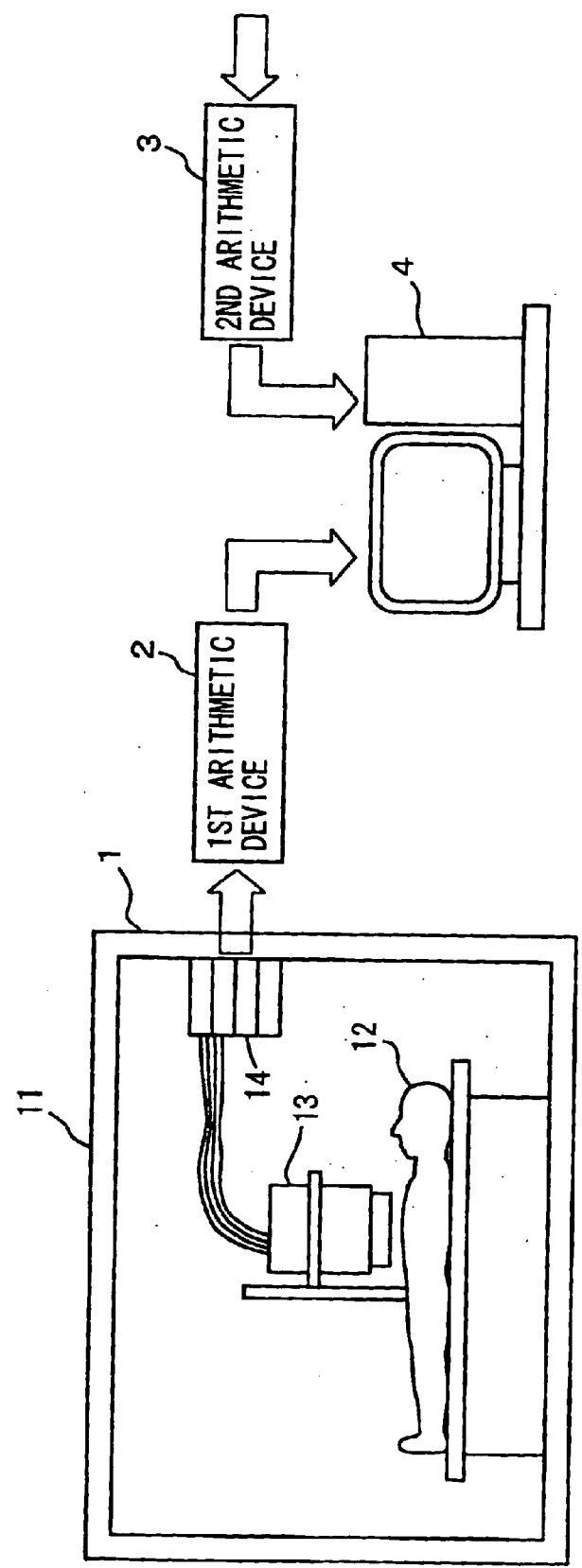
FIG. 2 is a block diagram more specifically showing the configuration of the FIG. 1 apparatus.

FIG. 2 is a block diagram more specifically showing the configuration of the magnetocardiographic diagnosis apparatus for a ventricular late potential of the first embodiment shown in FIG. 1.

As shown in FIG. 2, magnetic field distribution measurement device 1 includes in a magnetic shield room (MSR) 11 a Dewar structure 13 incorporating a SQUID magnetometer and arranged on the chest of a subject 12 to provide a non-contact magnetic measurement, and a magnetic field distribution data operation unit 14.

In Dewar structure 13 is provided a low-temperature environment filled with liquid helium to provide superconductance, and in the environment is accommodated a SQUID magnetometer configured of a detector coil formed of superconductor.

Figure 3:
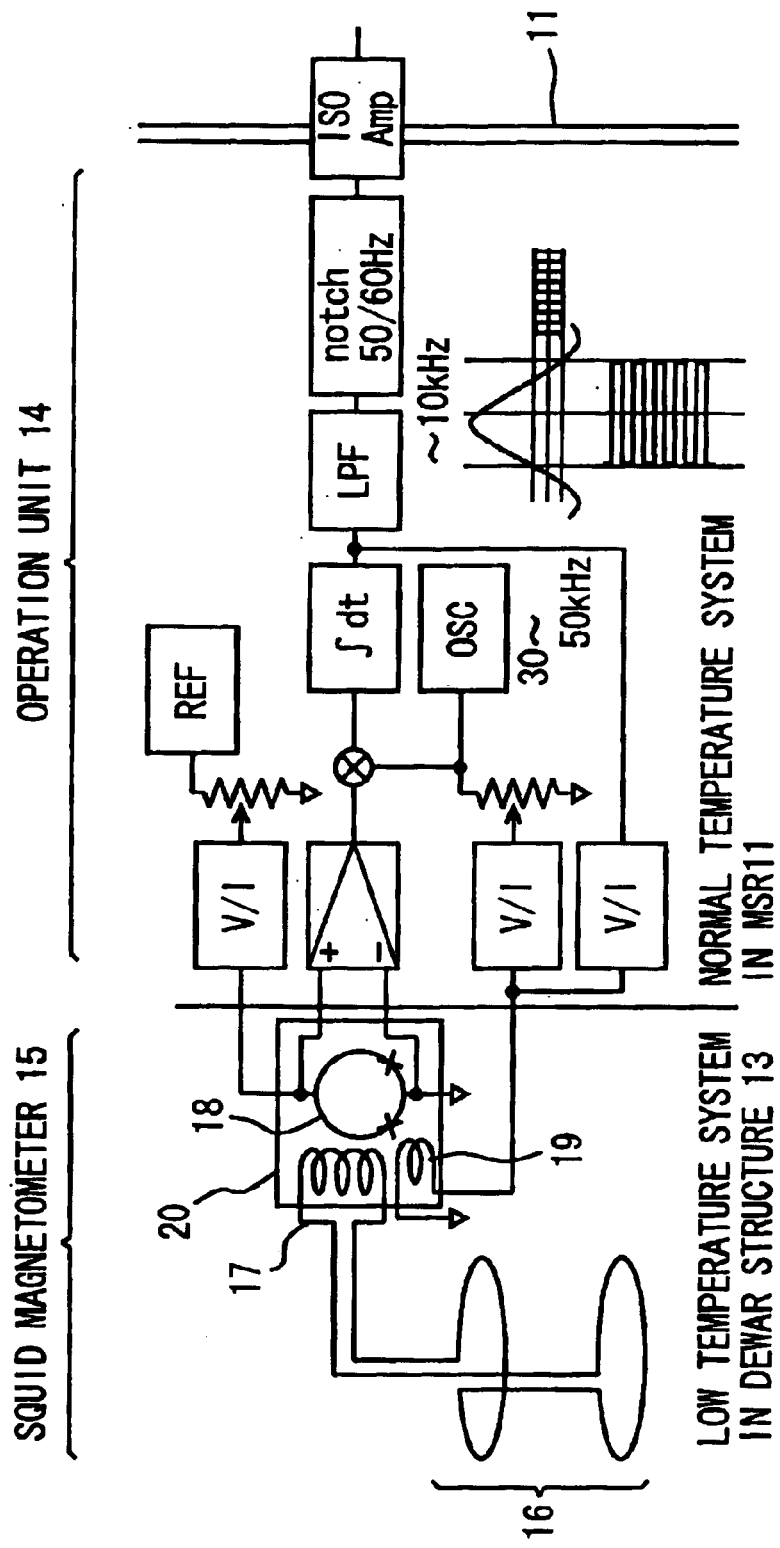
FIG. 3 is a block diagram showing in detail a configuration of a magnetic field distribution measurement device shown in FIG. 2.

FIG. 3 is a block diagram more specifically showing a SQUID magnetometer 15 arranged in an ultra low temperature system provided in Dewar structure 13 arranged in MSR 11 shown in FIG. 2, and operation unit 14 arranged in MSR 11 of a normal temperature system.

Note that the configuration shown in FIG. 3 is that for a single channel for measuring magnetic data of a single point on a subject's chest. As will be described hereinafter, in the present invention, on a subject's chest at a plurality of coordinates a magnetic field is measured, i.e., a multi-point, simultaneous magnetic measurement is provided. Accordingly, MSR 11 of FIG. 2 would have therein the 1-channel configuration of FIG. 3 for each of channels required for a measurement.

With reference to FIG. 3, for a single channel a SQUID magnetometer generates magnetic data, as described hereinafter.

SQUID magnetometer 15 includes a pickup coil 16 formed of superconductor for detecting a magnetic field generated from a surface of the chest of a subject. When pickup coil 16 captures a magnetic field, a current flows and drawn in by a coil 17 to create a magnetic field in an Nb shield 20.

Consequently, a magnetic field varying linearly relative to that created in Nb shield 20 is formed in a superconducting loop 18. Voltages of opposite ends of superconducting loop 18 are detected by an amplifier of operation unit 14 provided in MSR 11 of the normal temperature system. Operation unit 14 adjusts a current flowing through a modulation coil 19 provided in Nb shield 20 so that a detected voltage can thus be free of variation.

More specifically, the detection of an electric field of a human body by a SQUID is not a direct measurement of a magnetic field generated. Rather, a so-called a zeropotential method is used to provide a feedback to allow a magnetic field in superconducting loop 18 to have a constant value (more specifically, a current flowing through modulation coil 19 is adjusted to control a magnetic field generated in modulation coil 19 so that superconducting loop 18 internally, constantly has a constant magnetic field) to allow operation unit 14 to convert to an electrical signal a magnetic field detected at pickup coil 16 and output the signal. Such a feedback technique is typically a well known technique referred to as a flux locked loop (FLL).

Such a SQUID magnetometer 15 and its operation unit 14 are well known and will not further be described.

As has been described previously, the configuration shown in FIG. 3 is that necessary for measuring magnetic data for a single channel and outputs an electrical signal corresponding to time-series magnetic data of a magnetic field measured on a front side of the chest of a subject at a single point.

In the present invention, as has been described previously, a large number of sensors (SQUID magnetometers) are arranged on a front side of the chest of a subject to measure a magnetic field on the front side at multiple points. A magnetic field varies with time and for example even during a period corresponding to a single heart beat a magnetic field that is measured at different sites exhibits different variations depending on the sites.

Figure 4:
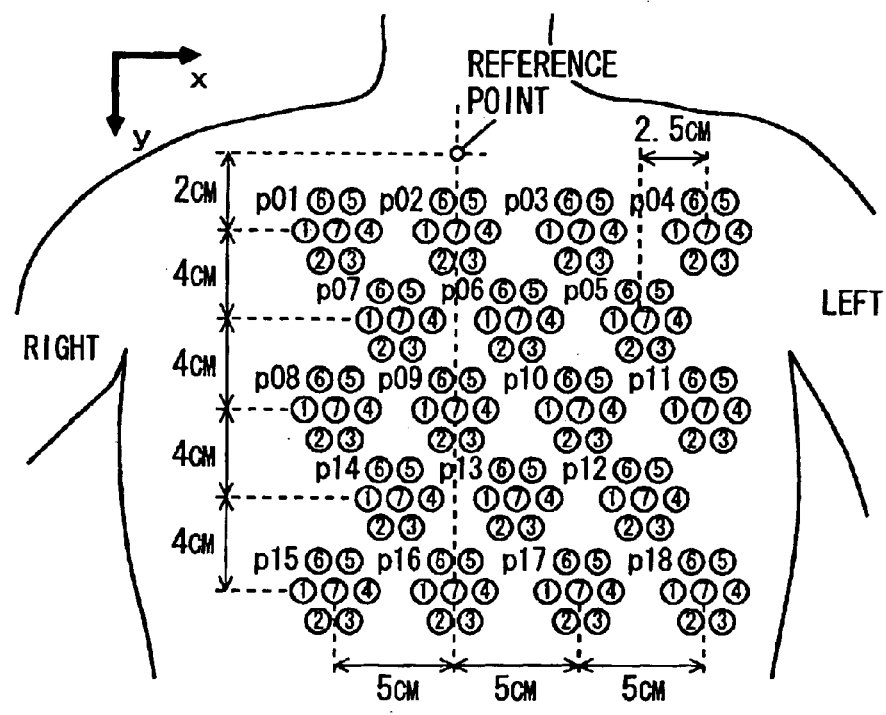
FIG. 4 shows by way of example an arrangement of a plurality of magnetic sensors on a front side of the chest of a subject.

FIG. 4 exemplarily shows an arrangement of a plurality of sensors (each corresponding to a SQUID magnetometer of a single channel) on a front side of the chest of a subject. Furthermore, FIG. 5 represents a group of time-series magnetic data representing a variation of a magnetic field for the period of a single heart beat that is obtained from the respective sensors of FIG. 4, as corresponding to their respective positions.

Figure 5:
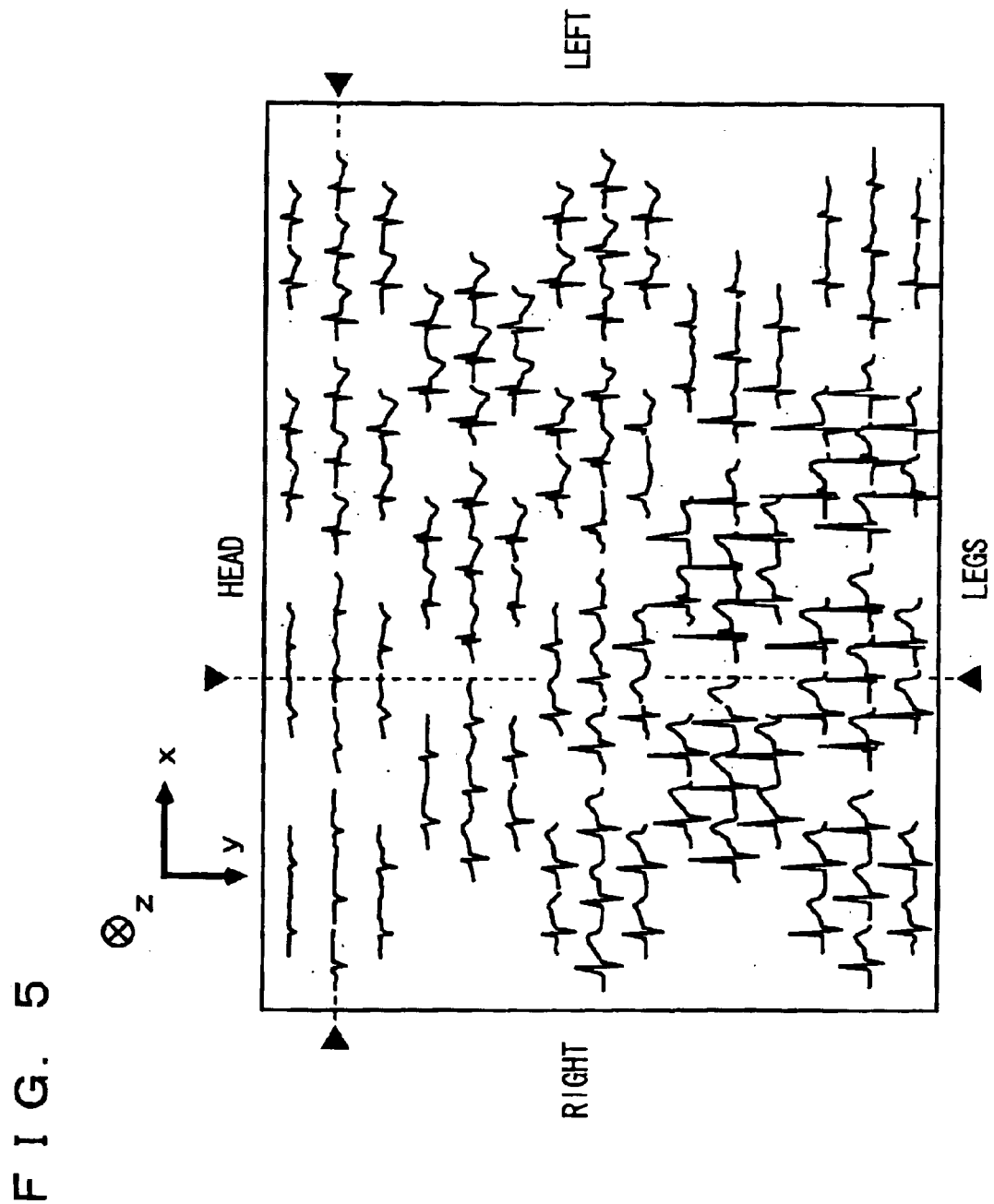
FIG. 5 represents time-series magnetic data obtained from the plurality of sensors shown in FIG. 4, respectively.

Magnetic field distribution measurement device 1 shown in FIG. 2 outputs a group of time-series magnetic data corresponding to a plurality of positions (coordinates) for measurement, as shown in FIG. 5. If a group of time-series magnetic data is captured with a particular time noted, it is difficult to graphically (diagrammatically) represent ridges and troughs representing a distribution in intensity of a magnetic field present at a specific time on a front side of a chest to be measured, and magnetic field distribution data represented in a contour map such as an atmospheric pressure represented in a weather chart is accordingly obtained. In this sense also, data output from magnetic field distribution measurement device 1 can be captured as time-series data of a distribution of a magnetic field on a front side of a chest.

A group of time-series, magnetic data such as output from magnetic field distribution measurement device 1, i.e., time-series magnetic field distribution data are fed to the first arithmetic device 2 of FIG. 2. The first arithmetic device 2 functions to obtain from magnetic field distribution data an electrical behavior in the chest, e.g., an intramyocardial excitation conduction rate.

From the time-series magnetic field distribution data generated by, magnetic field distribution measurement device 1 the first arithmetic device 2 obtains three-dimensional information of an electrical behavior in a human body at a part to be measured (a heart in the present invention), e.g., an intramyocardial excitation conduction rate, as described hereinafter.

The first arithmetic device 2 approximates time-series, magnetic field distribution data generated by magnetic field distribution measurement device 1. In doing so, one or more small current element pieces (i.e., current dipoles) are used. More specifically, the small current element pieces are scattered in a measured magnetocardiographic distribution and a well known analysis methodology is employed to determine a parameter (positional information and electric-current vector) of each small current element piece with respect to a respective point for measurement. Such an analysis methodology using current dipoles is a well known technique, for example as specifically disclosed in Japanese Patent Laying-Open No. 5-157735, and it will not be described herein in detail.

If the above analysis methodology is used to determine a parameter (i.e., position and electric current's direction) of each small current element piece in a magnetocardiographic distribution that corresponds to a specific time point, then by observing the parameter's chronological variation, information regarding a current's conduction rate can be obtained.

The first arithmetic device 2 initially generates data representing such a chronological variation of the position and electric current's direction of a small current element piece, as described above, and feeds the data to display device 4 at one input. The first arithmetic device 2 also uses the chronological variation to calculate an intramyocardial excitation conduction rate and the result may be generated in the form of numerical data and furthermore may be generated in the form of image data visibly representing the rate by an arrow having a length.

Thus the first arithmetic device 2 generates from the magnetic field distribution data generated by magnetic field distribution measurement device 1 a variety of forms of time-series data representing an intramyocardial excitation conduction rate to be analyzed, and input the generated time series data to display device 4 at one input.

The second arithmetic device 3 shown in FIG. 2 receives image data of a plurality of sliced images (for example a dozen of such images obtained at a pitch of five millimeters) of the chest of the same subject that are previously taken using another tomographic analysis apparatus (not shown) such as MRI, x-ray CT, echocardiography or myocardial SPECT with an electrocardiography synchronization trigger applied.

The second arithmetic device 3 processes (interpolates) the data of the plurality of sliced images and subjects the data to three-dimensional, perspective conversion from a predetermined point of view to generate second data representing an anatomical image. Thus forming a three-dimensional, anatomical image from a plurality of sliced images is a well-known technique, for example as specifically disclosed in Japanese Patent Laying-Open No. 11-128224 and International Publication WO 98/15226, and will not be described specifically.

Thus the second arithmetic device 3 generates the second data representing a three-dimensional, anatomical image of the chest of the same subject in a vicinity of his/her heart and feeds the second data to display device 4 at the other input.

Display device 4 of FIG. 2 superimposes on a three-dimensional, anatomical image of a subject's chest based on the second data from the second arithmetic device 3 an image based on the first data from the first arithmetic-device 2 and representing a chronological variation of a position and a direction of a current of a small current element piece in myocardium.

Figure 6:
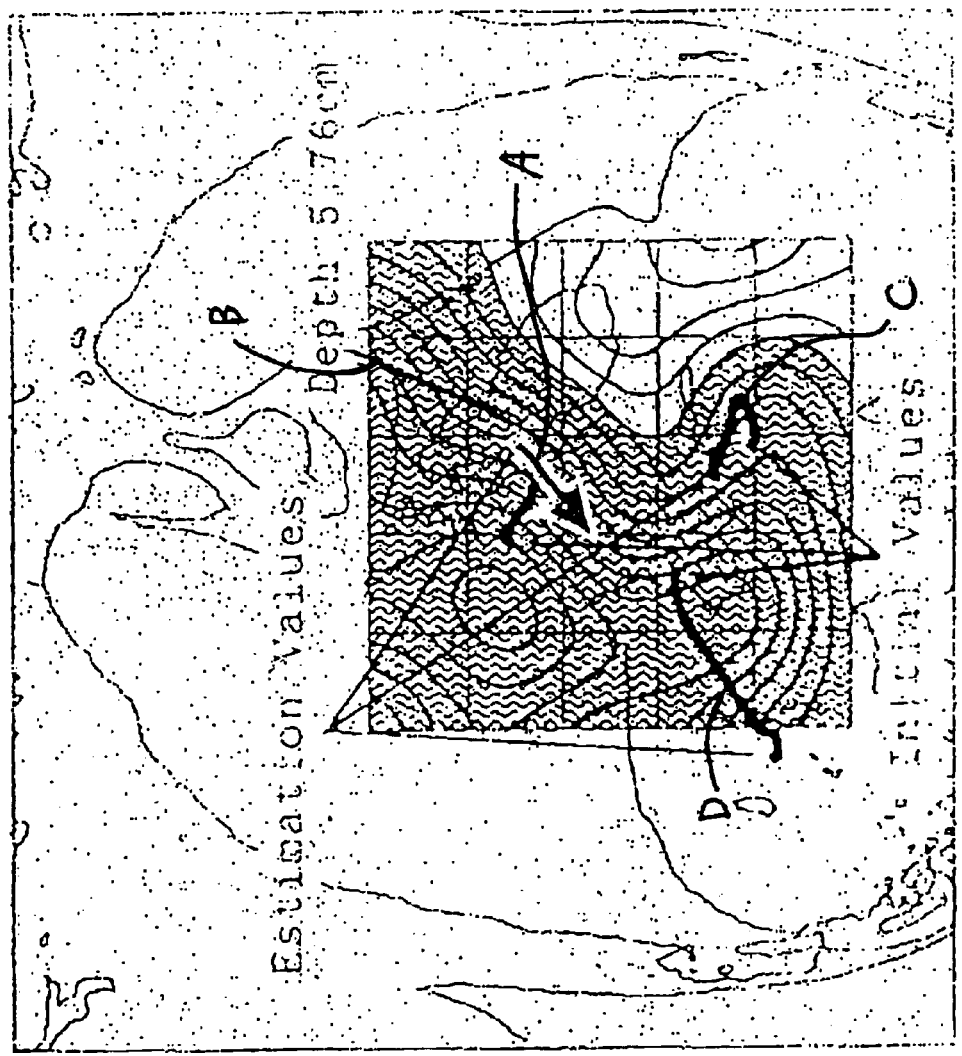
FIG. 6 shows an example of a three-dimensional, anatomical image displayed on a display device 4.

FIG. 6 shows a manner of displaying a position and direction of a small current element piece representing an intramyocardial excitation current in a magnetocardiographic distribution at a specific time point, and an excitation conduction path before that time point is arrived at, as superimposed on a three-dimensional, anatomical image displayed by display device 4.

FIG. 6 is a three-dimensional image obtained by interpolating approximately five tomographic images obtained by slicing a subject's chest at a pitch of five millimeters, for example. A depth of a displayed image is difficult to represent by drawing. It is, however, intended to show a stereoscopic, anatomical image providing a sense of a depth that is formed by combining a plurality of sliced images.

In FIG. 6 an arrow A indicates the position and direction of a small current element piece representing an intramyocardial excitation current corresponding to the time point and its length represents the magnitude of the current. Furthermore, thick lines B, C, D represent a tracing of an intramyocardial excitation conduction path obtained by approximating a magnetic field of a heart by means of a small current element piece and more specifically, correspond to the small current element piece's positional variation chronologically linked together.

As such, for a part in myocardium with a low excitation conduction rate a small current element piece has its position varying with time to form a dense tracing, and for a part in myocardium with a high excitation conduction rate a small current element piece has its position varying with time to form a sparse tracing. As such, the sparseness/denseness of the position of a small current element piece configuring each of thick lines B, C, D representing an excitation conduction path displayed on a screen, allows their respective, intramyocardial excitation conduction rates to be visually recognized.

Furthermore, as has been described above, the first arithmetic device 2 may calculate the exact, each intramyocardial excitation conduction rate and display device 4 may display it numerically.

Thus on a perspective, three-dimensional, anatomical image an intramyocardial excitation conduction rate can be displayed for each excitation conduction path to allow doctors to correctly understand a relative, positional relationship of a part in myocardium having a ventricular late potential, i.e., a part in myocardium providing un-uniform conduction of excitation on the anatomical image.

Figure 7:
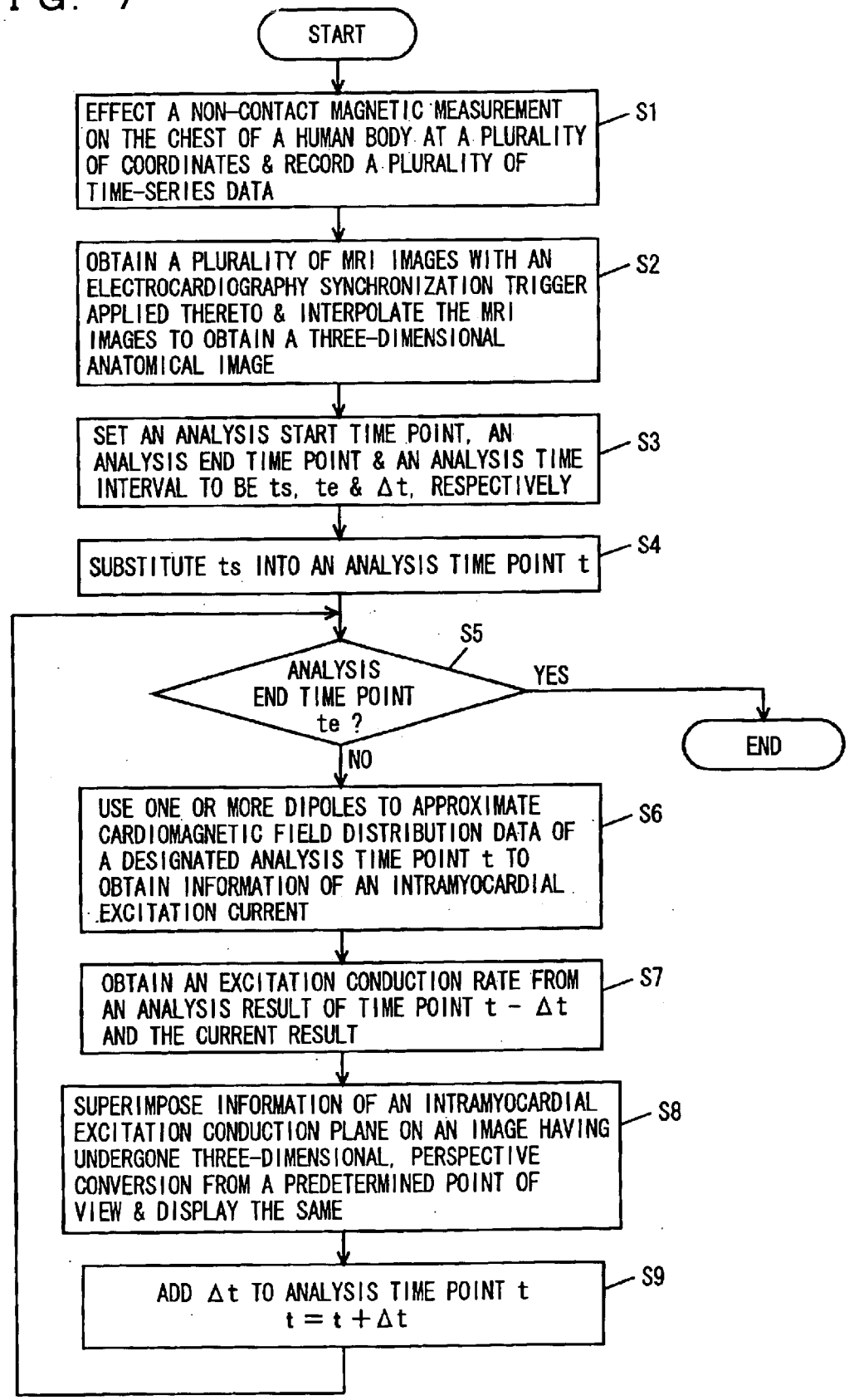
FIG. 7 is a flow chart for illustrating an operation of the magnetocardiographic diagnosis apparatus in accordance with the present invention in the first embodiment.

FIG. 7 is a flow chart of a method effected by the magnetocardiographic diagnosis apparatus of the first embodiment to identify a part in myocardium providing un-uniform conduction of excitation.

In FIG. 7 initially at step S1 magnetic field distribution measurement device 1 is used to provide non-contact magnetic measurement on the chest of a human body at a plurality of coordinates, generate a plurality of time series data, and record the data if necessary.

Then at step S2 a plurality of MRI images taken with an electrocardiography synchronization trigger applied are interpolated by the second arithmetic device 3 (i.e., subjected to three-dimensional, perspective conversion from a predetermined point of view) to obtain a three-dimensional, anatomical image.

Then at step S3 an analysis start time point, an analysis end time point and an analysis time interval are set to be $t_s$, $t_e$ and $\Delta t$, respectively.

Then at step S4 analysis start time point $t_s$ is substituted into an analysis time point t to start an analysis. Then at step S5 until analysis time point t reaches analysis end time point $t_e$ the following process is effected.

More specifically at step S6 the first arithmetic device 2 approximates magnetocardiographic distribution data corresponding to a designated analysis time point t, with one or a plurality of small current element pieces, to obtain data of the location, direction and magnitude of an excitation current in myocardium.

Then at step S7 the data of the location, direction and magnitude of the intramyocardial excitation current at time point t−Δt, as obtained at step S6 of the previous loop preceding by time Δt, is compared to the data corresponding to time point t, as obtained at step S6 of the current loop, and an intramyocardial excitation conduction rate is calculated.

Then at step S8 display device 4 displays data representing an intramyocardial excitation conduction rate, as superimposed on an anatomical image having undergone a three-dimensional, perspective conversion from a predetermined point of view.

Then at step S9 Δt is added to analysis time point t.

Steps S6–S9 are repeated until a decision is made at step S5 that analysis time point t has reached analysis end time point $t_e$. When it reaches analysis end time point $t_e$ display device 4 terminates displaying data representing the intramyocardial excitation conduction rate superimposed on the anatomical image.

Thus in the first embodiment an image representing an intramyocardial excitation conduction rate obtained from a SQUID magnetometer obtaining a non-invasive magnetic measurement on a subject's chest can be superimposed on a three-dimensional, anatomical image and thus displayed to allow a doctor to three-dimensionally identify the anatomical, positional relationship, size and geometry of a part in myocardium having a ventricular late potential, i.e., a part in myocardium providing un-uniform conduction of excitation that might cause ventricular tachycardia.

In particular, if high frequency catheter cauterization is used to provide a treatment, it can previously, significantly narrow down a region to be electrophysiologically tested using a catheter and a test conducted while radioscopy is provided can be conducted in a significantly reduced period of time. Consequently, doctors and radiographers can avoid significantly large annual doses of x-ray exposure.

Furthermore, using the method of identifying a part in myocardium providing un-uniform conduction of excitation, as described in the first embodiment, together with high frequency catheter cauterization allows a less invasive medical operation to be used to treat ventricular tachycardia and thus further alleviate a burden on patients.

Second Embodiment

In the first embodiment, forming an anatomical image entails obtaining a large number of tomographic images of a subject and a test employing MRI, x-ray CT or the like is accordingly, previously conducted. This results in an increased number of tests and an increased burden on patients and also an obstacle to a treatment directly linked to a test.

The present invention in a second embodiment can provide a magnetocardiographic diagnosis apparatus for ventricular late potential and a method of identifying a part in myocardium providing un-uniform conduction of excitation that are capable of eliminating the formation of an anatomical image to conduct a reduced number of tests and carry out a diagnosis and a test such that they are directly linked.

Figure 8:
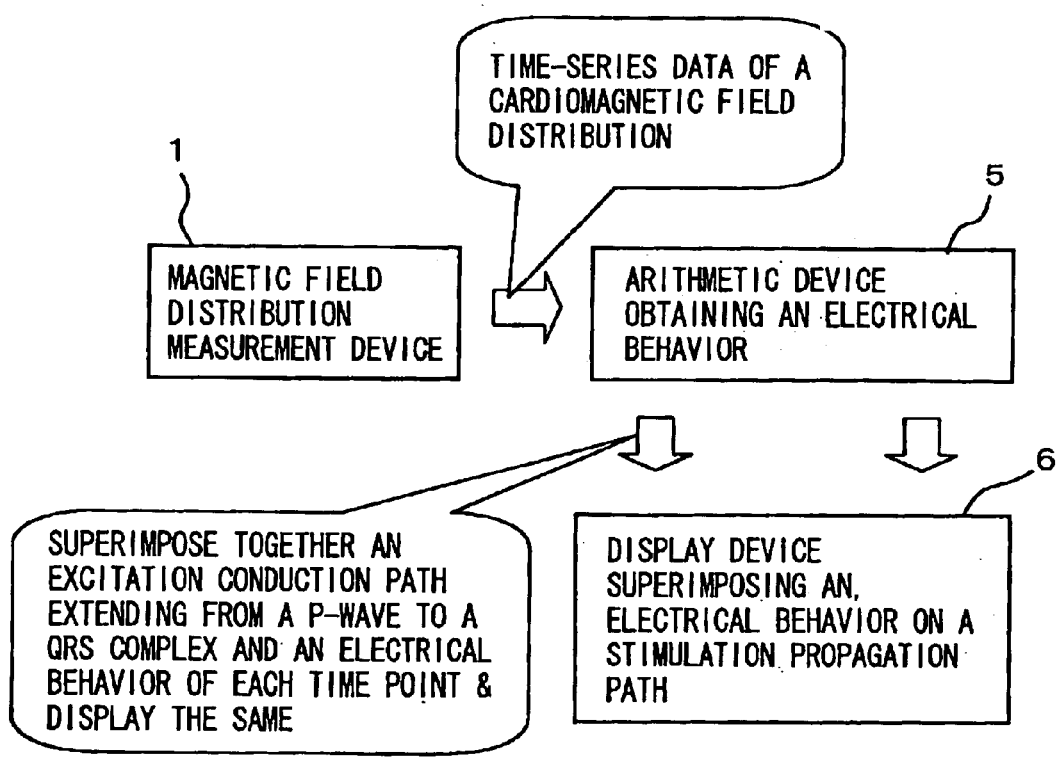
FIG. 8 is a functional block diagram schematically showing a configuration of a magnetocardiographic diagnosis apparatus for ventricular late potential in accordance with the present invention in a second embodiment.

FIG. 8 is a functional block diagram schematically showing a configuration of the magnetocardiographic diagnosis apparatus for ventricular late potential in the second embodiment.

With reference to FIG. 8, magnetic field distribution measurement device 1 will not be described as it has been described in the first embodiment.

Magnetic field distribution measurement device 1 generates time-series, magnetic field distribution data and outputs the data to an arithmetic device 5 which in turn uses the received time-series, magnetic field distribution data and employs the aforementioned analysis technique using a current dipole to generate data regarding an intramyocardial, three-dimensional electrical behavior, e.g., an intramyocardial excitation current. Arithmetic device 5 then uses the generated data of the excitation current to superimpose data representing a ventricular, intramyocardial excitation (stimulation) conduction path of a period corresponding to that from an electrocardiographically represented P wave to an electrocardiographically represented QRS complex and data representing an intramyocardial excitation conduction rate on each other and outputs the same to display device 6.

Display device 6 superimposes an image representing the intramyocardial excitation conduction rate represented by the data generated by arithmetic device 5, on a three-dimensional image of the excitation conduction path also obtained by arithmetic device 5 and corresponding to the period from the P wave to the QRS complex, and displays the same. Consequently, such an anatomical image as used in the first embodiment can be dispensed with to three-dimensionally identify a positional relationship of a part in myocardium providing un-uniform conduction of excitation.

Figure 9:
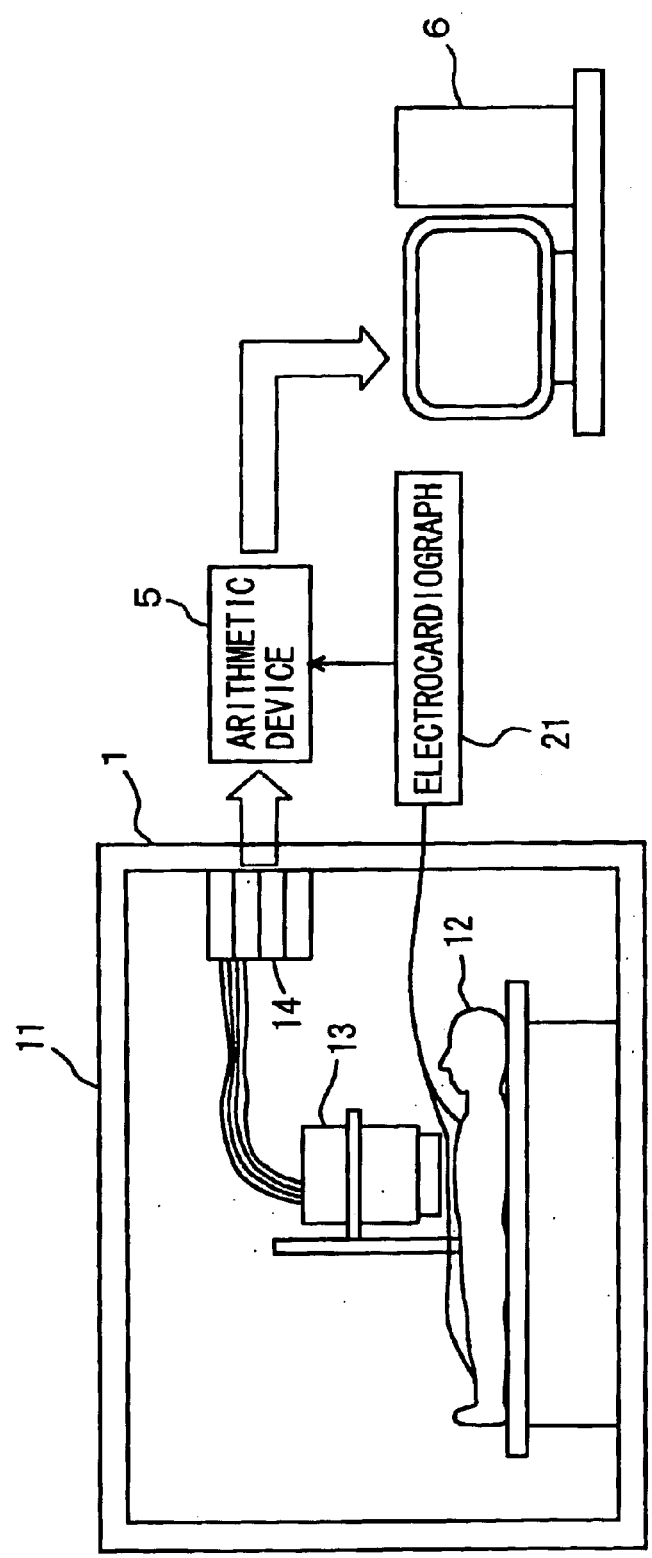
FIG. 9 is a block diagram more specifically showing the configuration of the magnetocardiographic diagnosis apparatus in accordance with the present invention in the second embodiment shown in FIG. 8.

FIG. 9 is a block diagram more specifically showing a configuration of the magnetocardiographic diagnosis apparatus of the second embodiment shown in FIG. 8.

With reference to FIG. 9, magnetic field distribution measurement device 1 will not be described as it is identical to that described with reference to FIGS. 2 and 3.

Magnetic field distribution measurement device 1 outputs time-series, magnetic field distribution data and outputs the data to arithmetic device 5 shown in FIG. 9. Arithmetic device 5 employs the analysis technique using a current dipole, as described above, to generate from time-series, magnetic field distribution data the data regarding an intramyocardial excitation current.

Subject 12 has his/her electrocardiogram recorded by an electrocardiograph 21 to allow measured electrocardiographic waveform data of subject 12 to be fed to arithmetic device 5.

Note herein that if the electrocardiographically represented waveform and the generated data regarding an intramyocardial excitation current, the electrocardiogram and an event occurring in the heart can also be correlated.

Figure 10A:
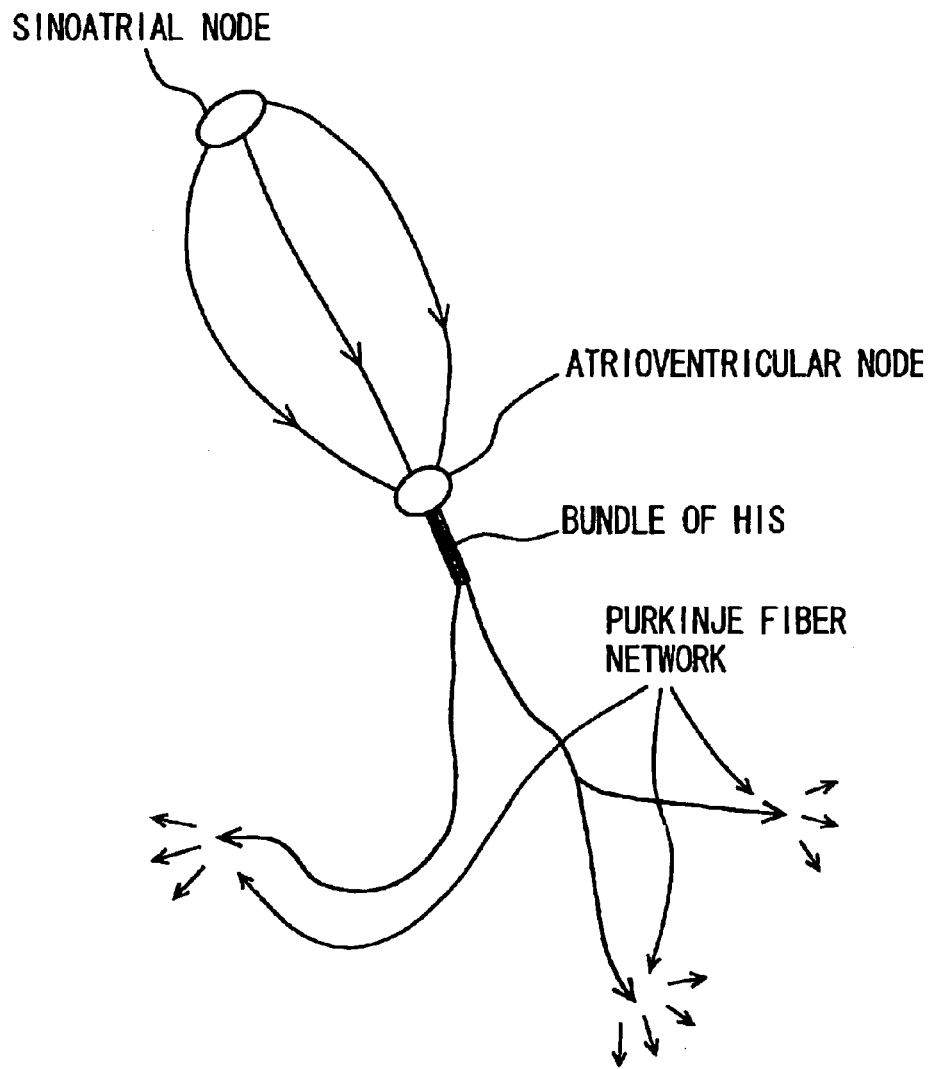
FIGS. 10A and 10B schematically show a normal stimulation conduction path in a heart and an electrocardiographically represented waveform.
Figure 10B:
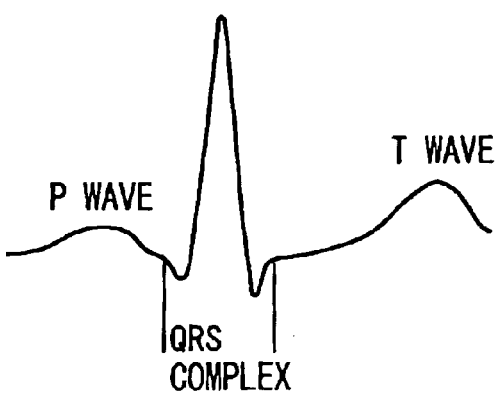

Reference will now be made to FIG. 10A schematically representing a normal stimulation conduction path in a heart and FIG. 10B representing an electrocardiographically represented waveform for a single heart beat.

With reference to FIGS. 10A and 10B, a sinoatrial node functions as a pacemaker determining a heart beat and it fires at predetermined intervals (a timing of a P wave of an electrocardiogram) to generate a pulse. This pulse is transmitted through a specific stimulation conduction path to an atrioventricular node and therein after a period of time elapses a pulse is transmitted through a bundle of His and a Purkinje fiber network to an underlying a ventricle and myocardial contraction erupts. This conduction of a stimulation from the bundle of His to the Purkinje fiber network corresponds to the period of the QRS complex in the electrocardiogram.

As such, by analyzing magnetocardiography related to the period from the P wave to the QRS complex, i.e., by analyzing an intramyocardial excitation current, arithmetic device 5 generates image data representing a stimulation conduction path serving as a normal route, as shown in FIG. 10A.

An image of a stimulation conduction path, such as shown in FIG. 10A, can be used in place of the anatomical image used in the first embodiment, as a template displayed. More specifically, a three-dimensional, anatomical image such as described in the first embodiment can be dispensed with if a stimulation conduction path of a normal route, as shown in FIG. 10A, is displayed, since a part in myocardium that exists in a neighboring ventricle and has a ventricular late potential, i.e., provides un-uniform conduction of excitation would be readily, anatomically correlated by a doctor and its location, size and geometry would be identified by the doctor.

Arithmetic device 5 shown in FIG. 9 generates data representing a generated intramyocardial excitation conduction rate, superimposed on a displaying of a stimulation conduction circuit as a template, such as described above. As has been described previously, by noting an image representing an intramyocardial excitation conduction rate, in a ventricle a part in myocardium providing un-uniform conduction of excitation or a part having a ventricular late potential can be found, and such image data can be combined with the aforementioned template image data and fed to display device 6.

Display device 6 shown in FIG. 9 uses the data received from arithmetic device 5 to display an image representing an intramyocardial excitation conduction rate, as superimposed on a normal stimulation conduction circuit serving as a template. Thus doctors can readily determine whether there is a condition allowing a reentry circuit to be readily formed in ventricular muscle.

FIG. 11 exemplarily shows a screen actually displayed by display device 6. It displays an image representing an intramyocardial excitation conduction rate for each excitation conduction path, superimposed on a normal stimulation conduction circuit serving as a template.

In FIG. 11, two arrows are shown, each indicating the position of an excitation conduction path approximated by a small current element piece (a current dipole). Each arrow has a length representing an excitation conduction rate.

A doctor would be able to refer to a positional relationship of a respective excitation conduction path relative to the normal stimulation conduction path serving as a template, as shown in FIG. 11, to provide an anatomical correlation and would also be able to refer to a difference in excitation conduction rate between excitation conduction paths to identify the location, size and geometry of a part in a ventricle that has a ventricular late potential, i.e., a part in myocardium that provides un-uniform conduction of excitation.

Figure 12:
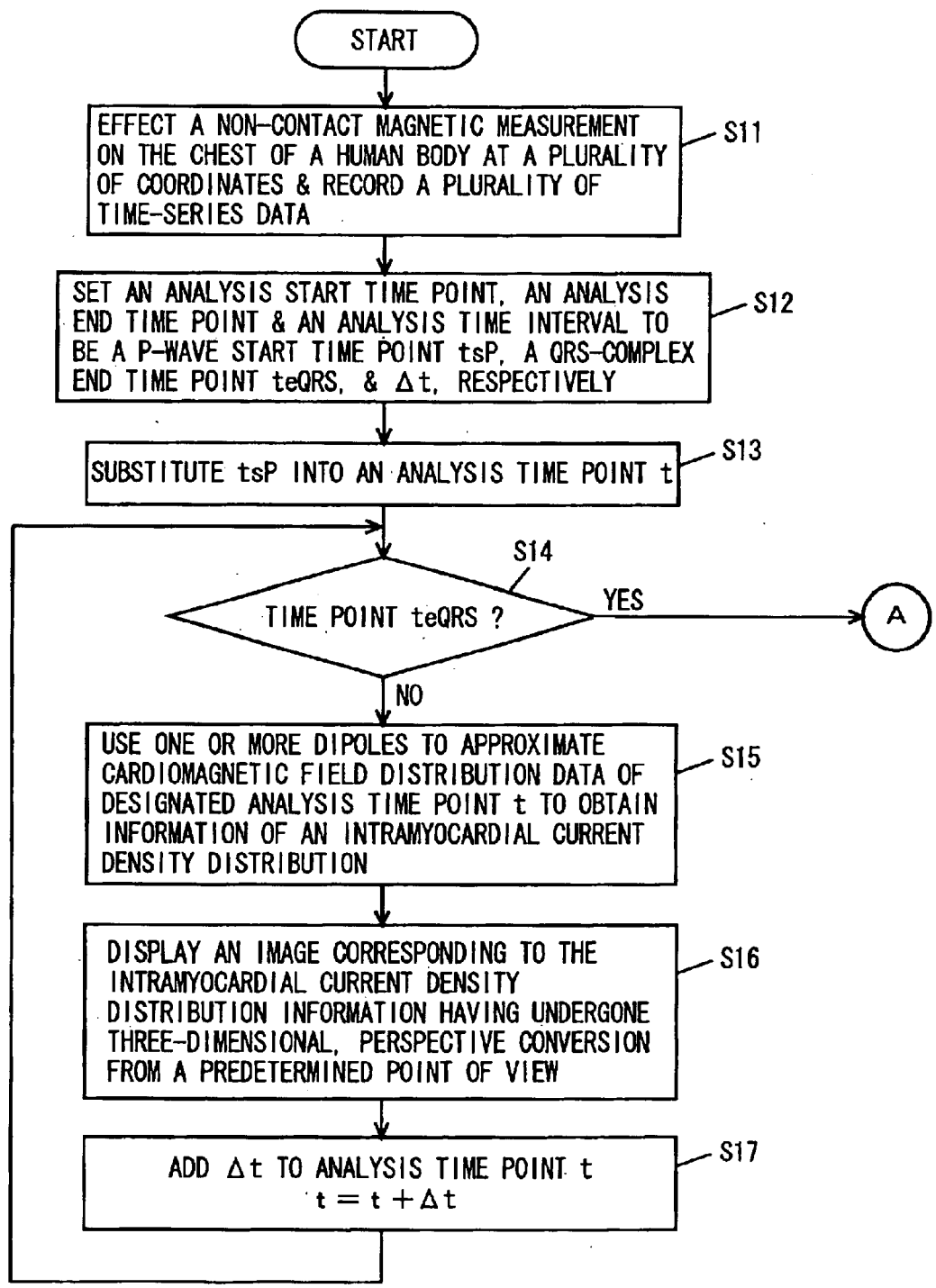
FIGS. 12 and 13 are a flow chart for illustrating first and second halves, respectively, of an operation of the magnetocardiographic diagnosis apparatus in accordance with the present invention in the second embodiment.
Figure 13:
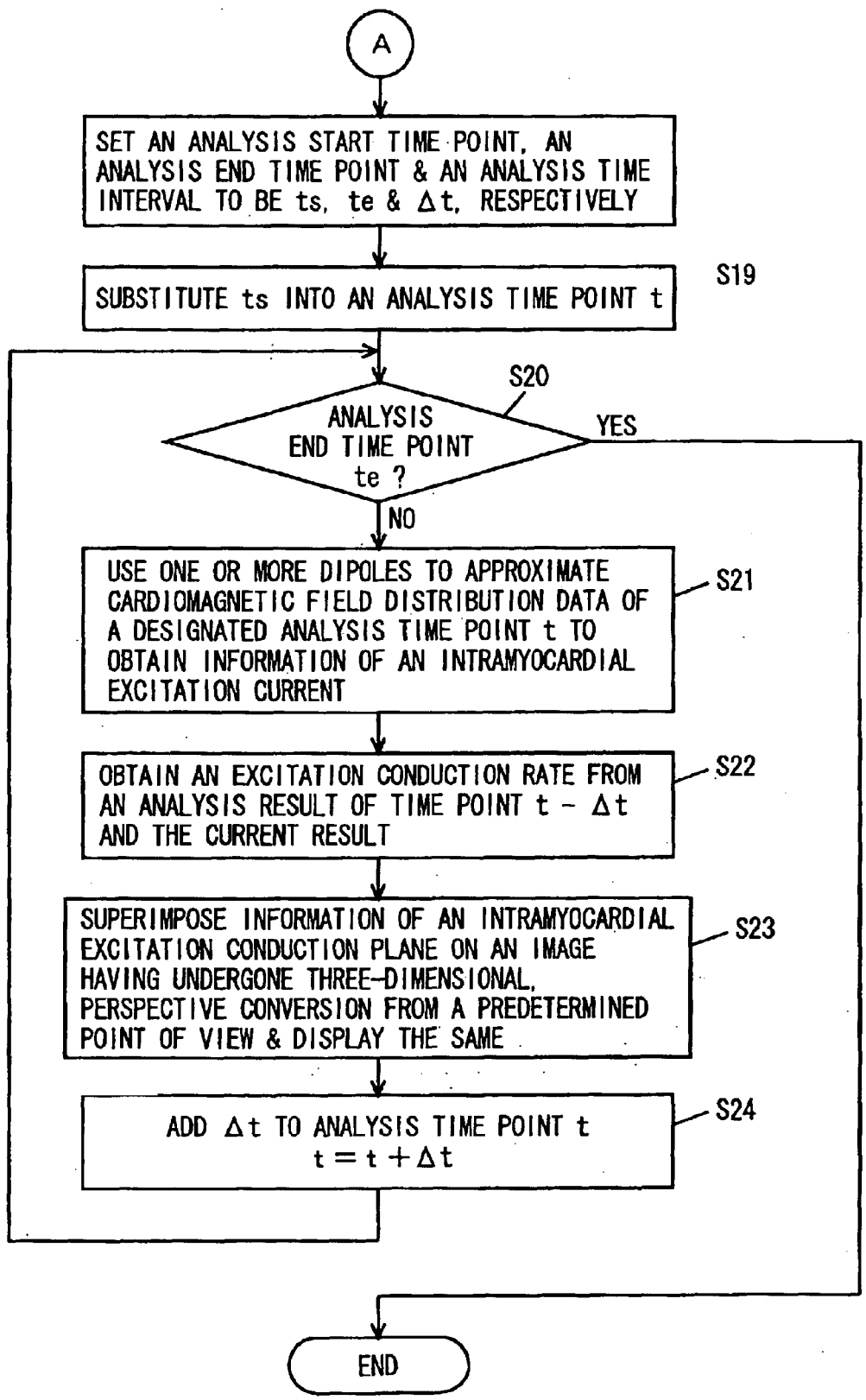

FIGS. 12 and 13 are a flow chart representing a method effected by the magnetocardiographic diagnosis apparatus of the second embodiment to identify a part in myocardium providing un-uniform conduction of excitation.

Initially, with reference to FIG. 12, at step S11 magnetic field distribution measurement device 1 is used to provide a non-contact magnetic measurement on the chest of a human body at a plurality of coordinates to generate and record a plurality of time-series magnetic data.

Then at step S12 an analysis start time point is set to correspond to an electrocardiographically represented P-wave start time point $t_{sP}$, an analysis end time point to an electrocardiographically represented QRS-complex end time point $t_{eQRS}$, and an analysis time interval to $\Delta t$.

Then at step S13 time point $t_{SP}$ is substituted into analysis time point t.

Then at step S14 until an analysis time reaches time point $t_{eQRS}$ the following steps S15–S17 are repeated.

More specifically at step S15 arithmetic device 5 approximates magnetocardiographic distribution data of a designated analysis time point t with one or more small current element pieces to obtain data regarding the location, direction and magnitude of an intramyocardial excitation current.

Then at step S16 the data of the intramyocardial excitation current obtained at step S16 undergoes three-dimensional, perspective conversion from a predetermined point of view and displayed in an image.

Then at step S17 $\Delta t$ is added to analysis time point t and the process returns to step S14 and a decision is made as to whether time point $t_{eQRS}$ has been reached. If so then it means that there has been obtained image data representing a stimulation conduction path corresponding to a normal route, as shown in FIG. 10A, as corresponding in an electrocardiographically represented waveform to the period from the P wave to the QRS complex.

Then the process proceeds with step S18, shown in FIG. 13, and an analysis start time point, an analysis end time point and an analysis time interval are set to be $t_s$, $t_e$ and $\Delta t$, respectively.

Then at step S19 analysis start time point $t_s$ is substituted into analysis time point t.

Then at step S20 until a decision is made that analysis time point t has reached analysis end time point $t_e$ the following steps S21–S24 are effected in a loop.

More specifically, at step S21 arithmetic device 5 approximate magnetocardiographic distribution data of designated analysis time t with one or more small current element pieces to obtain data regarding the location, direction and magnitude of an intramyocardial excitation current.

Then at step S22 the data of the location, direction and magnitude of the intramyocardial excitation current at time point t−Δt, as obtained at step S21 of the previous loop preceding by time Δt, is compared to the data corresponding to time point t, as obtained at step S21 of the current loop, and an intramyocardial excitation conduction rate is calculated.

Then at step S23 display device 4 displays data representing an intramyocardial excitation conduction rate, as superimposed on an image of a normal stimulation conduction path having undergone a three-dimensional, perspective conversion from a predetermined point of view.

Furthermore at step S24 Δt is added to analysis time point t and the process returns to step S20 and a decision is made as to whether analysis end time $t_e$ has been reached. Thus data representing an intramyocardial excitation conduction rate is superimposed on and displayed together with an image of a stimulation conduction path (FIG. 10A) obtained through the FIG. 12 flow chart.

Thus in the second embodiment an image representing an intramyocardial excitation conduction rate obtained from a SQUID magnetometer obtaining a non-invasive magnetic measurement on a subject's chest can be superimposed on a normal stimulation conduction path serving as a template and it can thus be displayed to eliminate the necessity of superimposing it on an anatomical image to allow a doctor to three-dimensionally identify the positional relationship, size and geometry of a-part in myocardium having a ventricular late potential, i.e., a part in myocardium providing un-uniform conduction of excitation that might cause ventricular tachycardia, as seen relative to a stimulation conduction path. As such the second embodiment can eliminate the necessity of previously conducting a test to obtain the anatomical image.

In particular, if high frequency catheter cauterization is used to provide a treatment, it can previously, significantly narrow down a region to be electrophysiologically tested using a catheter and a test conducted while radioscopy is provided can be conducted in a significantly reduced period of time. Consequently, doctors and radiographers can avoid significantly large annual doses of x-ray exposure.

Furthermore, using the method of identifying a part in myocardium providing un-uniform conduction of excitation, as described in the second embodiment, together with high frequency catheter cauterization allows a less invasive medical operation to be used to treat ventricular tachycardia and thus further alleviate a burden on patients.

Note that in the second embodiment, in creating image data of a normal stimulation conduction path displayed as a template a current dipole is used to approximate an excitation conduction path. Such an image of a normal stimulation conduction path can be obtained by operating operation unit 5 to obtain an intramyocardial current density distribution from time-series, magnetic field distribution data generated by magnetic field distribution measurement device 1, and the intramyocardial current distribution density can be obtained from the time-series, magnetic field distribution data by employing synthetic aperture magnetometric (SMA), multiple signal classification (MUSIC) or other similar, various techniques. SAM and MUSIC have been studied and developed for example in the fields of radar and sonar and are well known techniques. However, they have hitherto been unapplied to magnetocardiographic diagnosis.

SAM and MUSIC are well known techniques and the algorithms using these techniques to obtain a current density distribution are significantly complicated, and they will not be described specifically. SAM is specifically described by Robinson S E and Vrba J, "*Functional Neuroimaging by Synthetic Aperture Magnetometry (SAM)*" in Proceedings of the 11th International Conference on Biomagnetism, "*Reent Advances in Biomagnetism,*" published by Tohoku University Press, 1999, pp. 302–305. MUSIC is specifically described by Hiroshi Hara and Shinya Kurishiro, "*Science of Cerebric Magnetism-SQUID Measurement and Medical Applications,*" published by Ohmsha, Jan. 25, 1997, pp. 117–119.

Thus in accordance with the-present invention an intramyocardial excitation conduction rate obtained through a non-invasive magnetic measurement on a patient's chest can be displayed visibly on a three-dimensional, anatomical image to allow three-dimensional identification of the location, size and geometry of a part having a ventricular late potential, i.e., a part in myocardium providing un-uniform conduction of excitation. This allows a non-invasive diagnosis of a part in myocardium providing un-uniform conduction of excitation or having a ventricular late potential that might cause ventricular tachycardia. As such, without imposing a burden on patients a rapid and safe test can be-conducted.

In particular, if high frequency catheter ablation is used to provide a treatment, it can previously, significantly narrow down a region to be electrophysiologically tested and thus effectively, significantly reduce doses of x ray radiation that are received by doctors and radiographers.

In accordance with the present invention in still another aspect a subject's intramyocardial excitation conduction rate can be superimposed on the same subject's normal stimulation conduction path from a sinoatrial node to a bundle of His-Purkinje fiber network to eliminate the necessity of obtaining an anatomical image to three-dimensionally identify the position of a part in myocardium providing un-uniform conduction of excitation, i.e., the localization and spread of a ventricular late potential. Furthermore, a test conducted to obtain the anatomical image can be eliminated and more economically efficient diagnosis can thus be provided.

Industrial Applicability

Thus in accordance with the present invention a magnetocardiographic diagnosis apparatus for a ventricular late potential and a method of identifying a part in myocardium providing un-uniform conduction of excitation can three-dimensionally identify the position, size and geometry of the part in myocardium providing un-uniform conduction of excitation. It is useful in non-invasively diagnosing a part in myocardium providing un-uniform conduction of excitation or having a ventricular late potential that might cause ventricular tachycardia.

What is claimed is:

1. A magnetocardiographic diagnosis apparatus for ventricular late potential, comprising:

a magnetic field distribution measurement device performing a non-contact magnetic measurement on a subject's chest at a plurality of coordinates to obtain a plurality of time-series magnetic data corresponding to said plurality of coordinates, and also using said plurality of time-series magnetic data to generate time-series magnetic field distribution data on said chest;

a first arithmetic device using said generated time-series magnetic field distribution data to generate data representative of a three-dimensional, intramyocardial, electrical behavior of said subject;

a second arithmetic device processing separately provided, tomographic, thoracic data of said subject to generate data representative of a three-dimensional anatomical image; and a display device displaying an image of said three-dimensional, intramyocardial, electrical behavior represented by said data generated by said first arithmetic device, as superimposed on said three-dimensional anatomical image represented by said data generated by said second arithmetic device, thereby capable of three-dimensionally identifying localization of a ventricular late potential attributed to intramyocardial, un-uniform excitation conduction, wherein said data generated by said first arithmetic device and representative of said three-dimensional, intramyocardial, electrical behavior is data representative of an intramyocardial excitation conduction rate and wherein said first arithmetic device approximates by means of one or more small current element pieces a part in myocardium corresponding to an excitation conduction path and calculates a temporal variation of a position of said small current element piece to generate data representative of an intramyocardial excitation conduction rate.

2. The apparatus of claim 1, wherein said first arithmetic device operates based on said calculated temporal variation of the position of said small current element piece to generate data representative of a difference in intramyocardial excitation conduction rate for each excitation conduction path.

3. A magnetocardiographic diagnosis apparatus for ventricular late potential, comprising:

a magnetic field distribution measurement device performing a non-contact magnetic measurement on a subject's chest at a plurality of coordinates to obtain a plurality of time-series magnetic data corresponding to said plurality of coordinates, and also using said plurality of time-series magnetic data to generate time-series magnetic field distribution data on said chest;

an arithmetic device using said generated time-series magnetic field distribution data to generate data representative of a three-dimensional, intramyocardial, electrical behavior of said subject; and a display device using the data generated by said arithmetic device to superimpose together an image representing a stimulation conduction path of said subject extending from a sinoatrial node to a bundle of His-Purkinje fiber network and an image representing a three-dimensional, intramyocardial, electrical behavior and display said images, thereby capable of three-dimensionally identifying localization of a ventricular late potential attributed to intramyocardial, un-uniform excitation conduction.

4. The apparatus of claim 3, wherein the data generated by said arithmetic device and representative of said three-dimensional, intramyocardial, electrical behavior is data representative of an intramyocardial excitation conduction rate.

5. The apparatus of claim 4, wherein said arithmetic device approximates by means of one or more small current element pieces a part in myocardium corresponding to an excitation conduction path and calculates a temporal variation of a position of said small current element piece to generate data representative of said intramyocardial excitation conduction rate.

6. The apparatus of claim 5, wherein said arithmetic device operates based on said calculated temporal variation of the position of said small current element piece to generate data representative of a difference in intramyocardial excitation conduction rate for each excitation conduction path.

7. A method of identifying a part in myocardium providing un-uniform excitation conduction, comprising the steps of:

performing a non-contact magnetic measurement on a subject's chest at a plurality of coordinates to obtain a plurality of time-series magnetic data corresponding to said plurality of coordinates and used to generate time-series magnetic field distribution data of said chest and generating first data representative of a three-dimensional, intramyocardial, electrical behavior of said subject from the generated time-series magnetic field distribution data;

processing separately fed, tomographic, thoracic image data of said subject to generate second data representative of a three-dimensional anatomical image; and displaying an image of said three-dimensional, intramyocardial, electrical behavior represented by said first data, as superimposed on said three-dimensional anatomical image represented by said second data, to allow three-dimensional identification of localization of a ventricular late potential attributed to intramyocardial, un-uniform excitation conduction.

8. The method of claim 7, wherein said three-dimensional, intramyocardial, electrical behavior represented by said first data is an intramyocardial excitation conduction rate.

9. A method of identifying a part in myocardium providing un-uniform excitation conduction, comprising the steps of:

performing a non-contact magnetic measurement on a subject's chest at a plurality of coordinates to obtain a plurality of time-series magnetic data corresponding to said plurality of coordinates and used to generate time-series magnetic field distribution data of said chest and generating first data representative of a three-dimensional, intramyocardial, electrical behavior of said subject from the generated time-series magnetic field distribution data;

processing separately fed, tomographic, thoracic image data of said subject to generate second data representative of a three-dimensional anatomical image; and displaying an image of said three-dimensional, intramyocardial, electrical behavior represented by said first data, as superimposed on said three-dimensional anatomical image represented by said second data, to allow three-dimensional identification of localization of a ventricular late potential attributed to intramyocardial, un-uniform excitation conduction, wherein said three-dimensional, intramyocardial, electrical behavior represented by said first data is an intramyocardial excitation conduction rate and the step of generating said first data uses one or more small current element pieces to approximate a part in myocardium corresponding to an excitation conduction path and calculates a temporal variation of a position of said small current element piece to generate data representative of said intramyocardial excitation conduction rate.

10. The method of claim 9, wherein the step of generating said first data uses said calculated temporal variation of the position of said small current element piece to generate data representative of a difference in excitation conduction rate for each excitation conduction path.

11. A method of identifying a part in myocardium providing un-uniform conduction of excitation, comprising the steps of:

performing a non-contact magnetic measurement on a subject's chest at a plurality of coordinates to obtain a plurality of time-series magnetic data corresponding to said plurality of coordinates and used to generate time-series magnetic field distribution data of said chest and generating data representative of a three-dimensional, intramyocardial, electrical behavior of said subject from the generated time-series magnetic field distribution data; and using said generated data to superimpose together an image representing a stimulation conduction path of said subject extending from a sinoatrial node to a bundle of His-Purkinje fiber network and an image representing a three-dimensional, intramyocardial, electrical behavior, and thus displaying said images to allow three-dimensional identification of localization of a ventricular late potential attributed to intramyocardial, un-uniform conduction of excitation.

12. The method of claim 11, wherein said three-dimensional, intramyocardial, electrical behavior represented by said data is an intramyocardial excitation conduction rate.

13. The method of claim 12, wherein the step of generating said data uses one or more small current element pieces to approximate a part in myocardium corresponding to an excitation conduction path and calculates a temporal variation of a position of said small current element piece to generate data representative of said intramyocardial excitation conduction rate.

14. The method of claim 13, wherein the step of generating said data uses said calculated temporal variation of the position of said small current element piece to generate data representative of a difference in said intramyocardial excitation conduction rate of each excitation conduction path.

* * * * *